United States Patent
Papaix et al.

(10) Patent No.: US 11,806,180 B2
(45) Date of Patent: Nov. 7, 2023

(54) ACTIVE PIXEL INTRAORAL RADIOLOGICAL IMAGE SENSOR AND ASSOCIATED IMAGE CAPTURE METHOD

(71) Applicant: Teledyne e2v Semiconductors SAS, Saint Egreve (FR)

(72) Inventors: Caroline Papaix, Quaix en Chartreuse (FR); Pierre Fereyre, Voreppe (FR); Raphaël Neri, Grenoble (FR)

(73) Assignee: TELEDYNE E2V SEMICONDUCTORS SAS, Saint Egreve (FR)

( * ) Notice: Subject to any disclaimer, the term of this patent is extended or adjusted under 35 U.S.C. 154(b) by 279 days.

(21) Appl. No.: 17/065,850

(22) Filed: Oct. 8, 2020

(65) Prior Publication Data
US 2021/0106295 A1    Apr. 15, 2021

(30) Foreign Application Priority Data
Oct. 10, 2019    (FR) ...................................... 1911273

(51) Int. Cl.
  *A61B 6/14*    (2006.01)
  *A61B 6/00*    (2006.01)
  *G01T 1/24*    (2006.01)

(52) U.S. Cl.
  CPC ............ *A61B 6/145* (2013.01); *A61B 6/4233* (2013.01); *G01T 1/247* (2013.01)

(58) Field of Classification Search
  CPC ....... A61B 6/145; A61B 6/4233; G01T 1/247; H04N 5/32
  See application file for complete search history.

(56) References Cited

U.S. PATENT DOCUMENTS 9,729,808 B2 *   8/2017   Fenigstein ............. H04N 5/378
10,524,757 B2 *  1/2020   Julien ..................... A61B 6/461
(Continued)

FOREIGN PATENT DOCUMENTS

GB        2574619 A  * 12/2019 .......... H04N 5/3741
WO   WO-2017121728 A1  *  7/2017 ................ A61B 6/14

OTHER PUBLICATIONS

Extended European Search Report for European Application No. 20200814.0 dated Nov. 11, 2020, 7 pages.

*Primary Examiner* — Christine S. Kim
(74) *Attorney, Agent, or Firm* — K&L Gates LLP

(57) ABSTRACT

The subject matter of the invention is an active pixel dental radiological image sensor, with integrated X-ray occurrence detection, which uses the pixels of the matrix to detect the start of an X-ray flash, by detecting the current produced by all the photodiodes in the matrix. A switching circuit MUX1 thus allows, in a first phase of detecting the start of an X-ray flash, a common connection node NC to be connected that corresponds to the drain of a photodiode initialisation transistor M1 at the input of a current-voltage conversion detection circuit DTX1, which provides as output a signal for detecting the start of an X-ray flash when the current produced by all the photodiodes of the matrix exceeds a predetermined threshold. The switching circuit MUX1 is then controlled to connect the common connection node NC of the pixels to a photodiode re-initialisation voltage source, VRS. In an alternative embodiment, some pixels of the matrix can be used to detect the end of an X-ray flash using the same principle, by injecting the current produced by the photodiodes of these pixels that is collected on a different common connection node, electrically isolated from the first, with the end of flash signal corresponding to a variation in this current, which falls below a predetermined threshold.

(Continued)

The active pixels can be of the three or more transistor type, in particular with five and more transistors.

12 Claims, 9 Drawing Sheets

(56) References Cited

U.S. PATENT DOCUMENTS

| | | |
|---|---|---|
| 2009/0109313 A1 | 4/2009 | Liu et al. |
| 2010/0213353 A1* | 8/2010 | Dierickx ................. G01T 1/247 250/214 R |
| 2016/0150165 A1* | 5/2016 | Grauer ................. H04N 5/3594 348/308 |
| 2017/0134677 A1 | 5/2017 | Nishihara |
| 2018/0008214 A1* | 1/2018 | Papaix ................. A61B 5/0088 |
| 2019/0025444 A1 | 1/2019 | Charrat et al. |

* cited by examiner

ACTIVE PIXEL INTRAORAL RADIOLOGICAL IMAGE SENSOR AND ASSOCIATED IMAGE CAPTURE METHOD

CROSS-REFERENCE TO RELATED APPLICATIONS

The present application claims priority from French Patent Application No. 1911273, filed on Oct. 10, 2019, the entire disclosure of which is hereby incorporated herein by reference.

FIELD OF THE INVENTION

The invention relates to the field of medical imaging, and further relates to an active pixel intraoral dental radiological image sensor using CMOS technology.

PRIOR ART

The structure of these active pixels is based on a photosensitive element (photodiode, photogate) associated with transistors that allow the various phases of image capture to be controlled: a phase of initialising photosensitive elements, before a phase of integrating charges, then a phase of reading the pixels. For this reading phase, for each pixel of a row of pixels of the matrix, a voltage level corresponding to the amount of charges accumulated in the pixel during the integration phase is transferred to a column conductor, by means of a transistor mounted as a voltage follower associated with a node for reading the pixel. Reading is then carried out by a reading circuit at the base of the column, which actually samples two voltage levels: the voltage level corresponding to the amount of charges accumulated in a node for reading the pixel and a voltage level corresponding to a re-initialisation level of the reading node, in order to subtract them from each other. This thus improves the signal-to-noise ratio (double sampling and subtraction of the correlated noises).

Dental radiological image capture usually occurs as follows: the sensor is placed in the mouth of the patient and is positioned behind the anatomical zone to be observed; the X-ray source is positioned and activated in order to emit an X-ray flash towards the active face of the sensor, through the biological tissues and materials of the anatomical zone to be radiographed. A sequencing circuit of the sensor triggers the image capture, upon detection of the beginning of the occurrence of the X-ray flash on the active face of the sensor. The X-rays that reach the active face of the sensor are converted into an electric signal by the pixels, directly or after conversion into rays visible by a scintillator, depending on the type of photodiodes. After reading the pixels, an image of the radiographed anatomical zone can be displayed on a computer screen, for example.

Detecting the start of the occurrence of the X-ray flash forms part of the measures required to be able to reduce the radiation doses applied to the patients. In terms of medical imaging, the recommendations of standardising bodies in terms of the radiation dose received by the patients and the practitioners are indeed very strict. In terms of the X-ray sources, for each image capture, it involves adjusting the intensity and the duration of the X-ray flash as a function of the morphology and of the age of the patient and of the anatomical zone to be radiographed, so that the dose of exposure is as low as possible and without any unnecessary loss, allowing a good quality image to be obtained in one take. In terms of the image sensor, it involves synchronising the phase of integrating charges in the best way possible with the effective exposure of the active face to the useful radiation, so that the signal-to-noise ratio is optimal with respect to the intensity and the duration of the radiation. If the integration phase starts too early, charges are accumulated that correspond to the dark current. If it starts too late, the useful signal is lost. In general, provision is also made to detect the end of the X-ray flash. This thus improves the signal-to-noise ratio (no integration of the dark current) and the reading phase is also triggered more quickly, which allows the speed and the efficiency of image acquisition to be improved, compared to a solution in which the integration duration would be pre-set to a set value, greater than a duration of the X-ray flash (adjustment data of the source).

The sensor thus must integrate a detection circuit, the purpose of which is to allow optimal setting of the start of the integration phase when the X-ray flash starts to occur on the active face of the sensor. The detection circuit generally uses bars of photodetectors that surround the matrix of pixels, horizontally and/or vertically. These bars of photodetectors are thus disposed immediately behind absorbent anatomical zones (teeth, gum), which compromises or delays the detection of the occurrence of the X-ray flash by the sensor. From this perspective, an optimal detection zone on the active face of the sensor could be the free zone (i.e. without an absorbent obstacle) between the upper and lower jaws of a patient, which corresponds to a detection band located in the middle of the matrix of pixels of the sensor, to the detriment of image capture pixels, requiring interpolation computations and filtering to reconstitute the corresponding image data, since the practitioners wish to see the complete image of the radiographed zone. This also means a loss of image quality, since the interpolation results in imprecision.

The use of pixels dispersed in the matrix as reference pixels is also known for detection, as described, for example, in U.S. Pat. No. 6,404,854. During detection, these reference pixels are each read individually, in a non-destructive manner (no re-initialisation between readings) for comparison to a threshold, and this occurs continually, until an image capture decision is taken when enough reference pixels have provided a signal above a certain threshold. A disadvantage of this solution is that it requires specific sequencing of these pixels. Yet above all, this solution is imperfect with respect to making the detection of the occurrence of the X-ray independent of the positioning of the sensor: it is not possible to avoid, according to the position of the sensor, most of the reference pixels from being located behind a highly absorbent zone, which delays the detection process.

Furthermore, and still to help to reduce the X-ray dose required for radiological image capture, a very low signal level needs to be able to be detected that marks the very start of exposure of the photosensitive zone to the radiation, in order to trigger the integration phase without losing useful information (or as little as possible). In other words, the intention is for the moment at which the detection signal is emitted to be very close to the actual arrival of the X-ray on the active face of the sensor. For these reasons, it is more advantageous to carry out direct detection of the current supplied by all the photodetectors, using a capacitive transimpedance amplifier, since the significant gain of the amplifier allows the detection threshold to be lowered, i.e. it is possible to determine the arrival of the X-ray flash earlier, and therefore begin to integrate earlier. Such amplifiers are well known and are commonly used for reading the pixels of infrared image sensors. Furthermore, in the field of medical radiology, patent application WO 2017/121728 describes a circuit for detecting the occurrence of an X-ray flash that is based on such an amplifier, for reading the current supplied by a set of detection photodiodes placed on either side of the matrix of pixels.

Therefore, there is a significant need for finding a technical solution to allow efficient detection of the occurrence of X-rays, independently of the position of the sensor, without sacrificing or losing the precision of image data, and that is simple to implement in the existing topologies, i.e. without having to completely reconsider the design and without impinging on the active image capture surface.

SUMMARY OF THE INVENTION

The subject matter of the invention is an active pixel dental radiological image sensor with integrated X-ray occurrence detection, which allows efficient detection of the detection of the occurrence of an X-ray, independently of the position of the sensor in the mouth of the patient, and that maximises the active surface (matrix) applied to the size of the sensor.

More specifically, the invention thus relates to an intraoral radiological image sensor using MOS technology comprising:
   a matrix of photosensitive pixels arranged in rows and columns, each pixel comprising a photodiode and transistors, including a photodiode initialisation transistor (M1) connected between a photodiode node of the pixel and a first connection node common to the pixels;
   a sequencing circuit supplying signals for controlling the transistors of the pixels for controlling an image capture sequence during exposure to an X-ray flash, comprising a phase of overall initialisation of the photodiodes of the pixels, a phase of integrating charges during an integration period and a phase of reading the pixels.

According to the invention, the sensor comprises a first coupling switch controlled by a first logic signal for connecting said first connection node to a signal input of a first current detection circuit or to a photodiode initialisation voltage source, whereby said first logic signal is respectively in a first logic state or a second logic state; and the sequencing circuit of the sensor being configured to control a phase of detecting, by said first detection circuit, the start of exposure to an X-ray flash for triggering the image capture sequence, comprising the following operations:
   a) commanding the photodiode initialisation transistors to switch to the on-state in all the pixels simultaneously; and
   b) establishing the first logic signal in said first logic state, the effect of which is to inject, at the signal input of the first detection circuit, a current collected on said first connection node originating from the photodiodes of the pixels; then
   c) establishing, when an output logic signal of the first detection circuit toggles from a first logic state to a second logic state, corresponding to the detection of an input current level above a predetermined threshold, the first logic signal in said second logic state, the effect of which is to couple said initialisation transistors, which are always in the on-state, to said initialisation voltage source, thus activating the phase of overall initialisation of the image capture sequence, for initialising the photodiodes before said integration phase.

In an improvement, the initialisation transistors of a set of pixels of the matrix are connected, not to said first connection node, but to a second connection node, which is electrically isolated from said first connection node, and the sensor comprises a second current detection circuit of the same type as said first detection circuit and controlled by the same clock signal, with an input signal that is coupled to said second connection node, and the initialisation transistors of the pixels of said set are in the on-state, at least until the detection of the end of exposure to the X-ray by the second detection circuit corresponding to a current injected at the input, collected from said second connection node that falls below a predetermined threshold; and
   upon detection of the end of exposure to the X-ray flash, stopping the phase of integrating the image capture sequence for initiating the reading phase.

Advantageously, a second coupling circuit is provided for connecting the second connection node to the signal input of the second detection circuit or to the initialisation voltage source as a function of a second control logic signal, which is configured in the sensor to configure the pixels of said set into end of exposure detection pixels or into image capture pixels.

According to one aspect of the invention, the gain of the capacitive transimpedance amplifier and/or the voltage threshold value of the comparator are adjustment parameters of the sensor adjusted in said first detection circuit and in said second detection circuit for respectively detecting the start and the end of an X-ray flash.

According to another aspect of the invention, the sequencing circuit is configured to trigger another image capture sequence applying the same integration duration and using the same pixels for the image capture as a preceding image capture sequence carried out during exposure to the X-ray flash and having supplied first image data, allowing measurement and subtraction of a dark noise on said first image data.

The sensor according to the invention is particularly applicable to active pixels with three or more transistors, in particular with five and more transistors.

According to one embodiment of the invention, a current detection circuit of the sensor comprises a capacitive transimpedance amplifier comprising a noninverting input connected to a common mode voltage and an inverting input, which forms the signal input, which is coupled to a common connection node of the pixels, said amplifier being controlled by a clock signal for periodically producing, at the signal output, a voltage ramp as a function of the level of the current injected at the signal input, which ramp is applied to a comparator for comparison to a voltage threshold value.

The invention also relates to a corresponding radiological image capture method.

BRIEF DESCRIPTION OF THE DRAWINGS

The invention will be better understood, and further advantages will become apparent, upon reading the detailed description of embodiments, which are provided by way of an example and are illustrated using the accompanying drawings, in which.

DETAILED DESCRIPTION

It is to be noted that the figures are simple diagrams illustrating the invention, which are not to scale. Only the functional elements or the signals required to understand the invention are shown. For the sake of clarity and of simplification, the same notations or references have been used throughout the description and in the figures to denote the same elements or similar elements.

Furthermore, in the following description, the terms "coupled" or "connected", when they are used, indicate a direct or indirect electrical connection; and the term "connected" indicates a direct electrical connection.

The invention relates to a radiological image sensor, and more specifically to an intraoral dental image sensor, using CMOS technology, using active pixels.

Figure 1:
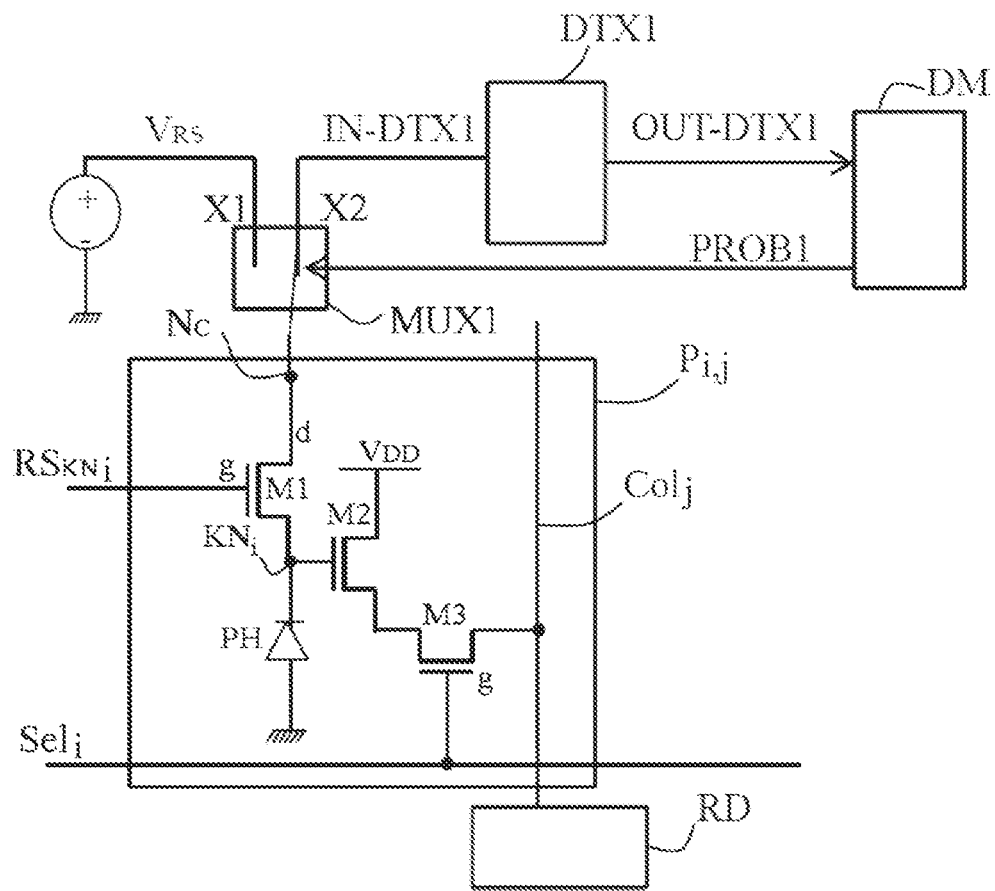
FIG. 1 is a functional block diagram of the detection of the start of an X-ray flash according to the invention adapted to an image sensor based on an active pixel structure of the three transistor (3T) type.

An active pixel is a pixel as illustrated by way of an example in FIG. 1, which comprises a photosensitive element, generally a photodiode PH and some transistors (MOS), which are all of the same type and are used as a switch (in the ON or OFF state) or a voltage follower, to control the various phases of the image capture sequence. Strictly speaking CMOS technology (combination of N and P transistors) more specifically relates to the electronics around pixels (control, reading, interface electronics, etc.).

The invention is more specifically illustrated within the context of an image sensor produced in a P-type doped semiconductor substrate, which is brought to a ground reference potential, generally a zero potential.

The photodiode PH preferably is of the "pinned" type, i.e. the junction PN is formed by an N-type doped region in a lightly doped substrate ($P^-$) and this region N (cathode) is overlaid with a highly doped P-type surface layer ($P^{++}$), brought to the ground reference potential of the substrate: this sets the potential of the wells N (region N) of the photodiode to a potential $V_{pin}$ (rest voltage of the photodiode), which only depends on the concentrations of the N and P dopants.

The transistors of the active pixel are of the N type. They are commanded to switch to the on-state (off or on) by applying a positive potential $V_{ON}$ to their gate g, which generally corresponds to the positive power supply voltage $V_{DD}$ of the electronic circuitry of the sensor. The level of this voltage $V_{DD}$, 3 volts, for example (FIG. 4), is a function of the CMOS technology that is used. They are commanded to switch to the OFF state (open or blocked) by applying a potential to their gate g that generally corresponds to the ground reference potential of the substrate (zero potential), or even to a more negative potential.

The logic control signals of the sensor can assume two logic values "0" or "1", respectively corresponding to the ground reference potential of the substrate and to $V_{DD}$.

The figures and the explanations reflect these conventions. A person skilled in the art knows how to easily transpose all this to active pixels with P-type MOS transistors.

For dental radiology, active pixels are generally used with three control transistors (3T), which promotes the storage capacity of the pixels. These pixels only allow images called "sliding shutter window" images to be produced, since the end of the integration period is offset row-by-row, coinciding with the sequential reading of the pixels, by scanning rows. With respect to the start of the integration period, within the context of dental radiology, it is the same for all the pixels, since it is synchronised upon detection of the occurrence of the X-ray flash (or more simply "X flash") on the active face of the sensor. The effective integration duration of the rows therefore increases with the scanning direction of the rows. The difference is small in terms of the total integration duration, but this causes a line effect in the image, which can be attenuated by image processing. This is well known.

The invention will be more specifically explained for a sensor using such a matrix of 3T pixels. However, it will be seen hereafter that it can be easily applied to structures with more transistors, which particularly have the advantage of allowing instantaneous image capture ("snapshot"), with a start and an end of integration that are identical for all the pixels, and more specifically to 5T structures, i.e. comprising (at least) 5 transistors. It is to be noted that within the context of the invention, the sensor is only sensitive to X-rays (by construction): therefore, it is blind to visible rays. In the integration period, it only integrates charges that correspond to the received X-ray.

Figure 2:
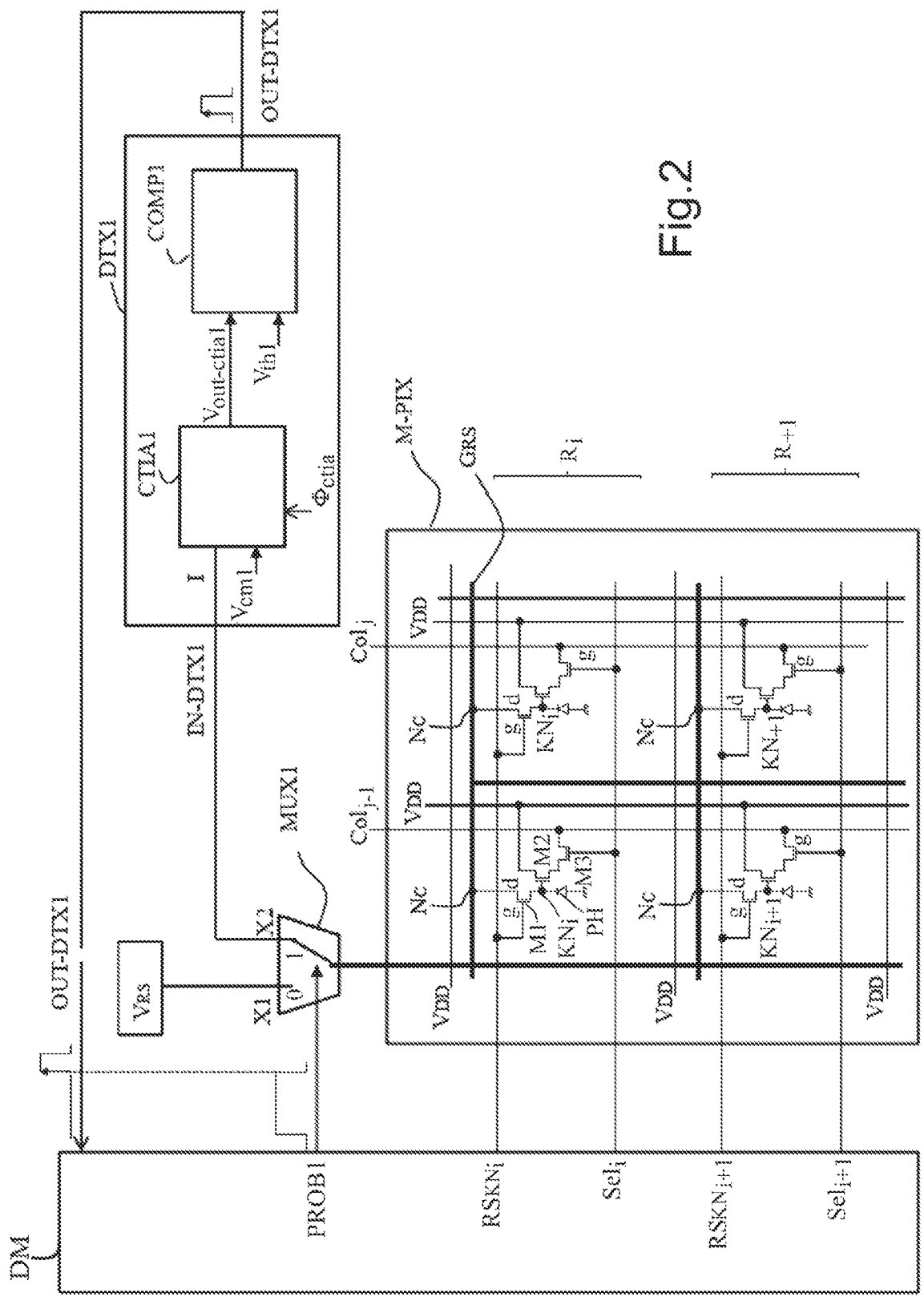
FIG. 2 is a block diagram of such a 3T pixel matrix image sensor including a device for detecting the start of exposure to an X-ray flash according to the invention.

FIGS. 1 and 2 illustrate the principle of detecting the start of an X-ray flash according to the invention in an image sensor based on a matrix M-PIX of 3T active pixels, which comprise, in the example, N rows and P columns of pixels. FIG. 1 shows this by focusing on a pixel of the matrix, and FIG. 2 shows the implementation of the invention in the sensor, which allows all the pixels of the matrix to be used, firstly to detect the start of exposure to the flash and, subsequently, to carry out the image capture sequence, upon detection of this start of a flash.

The pixel $P_{ij}$ (FIG. 1) located in the matrix on the row of pixels $R_i$ of rank i and on the column of pixels $Col_j$ of rank j, comprises:

- a photodiode PH (preferably of the "pinned" type), connected between a photodiode node $KN_i$ (cathode) and the reference ground voltage;
- a photodiode initialisation transistor M1 connected to the photodiode node $KN_i$ that receives, on its gate g, a signal $RSz_{KN_i}$ for initialising the row of pixels of rank i for commanding the discharge of the charges (electrons) accumulated in the photodiode towards a reference voltage source VRS (also called photodiode initialisation voltage hereafter);
- a transistor M2 mounted as a voltage follower, the gate of which is connected to the photodiode node $KN_i$ (capacitive), which converts the charges accumulated in the photodiode PH into a voltage level that is transferred to the column conductor Col$_j$, when the pixel is selected for reading; and a transistor M3 for selecting the reading pixel, connected in series between the transistor M2 and a column conductor Col$_j$ connected to a reading circuit RD, and which receives, on its gate g, a signal Sel$_i$ for selecting reading of the row of pixels With respect to the notation: KN$_i$ denotes the photodiode node of the pixels of the row i of rank of row. This allows this node to be easily associated with the photodiode re-initialisation signal of each row, denoted RS$_{KN_i}$.

The reading circuit RD allows, for each of the pixels of the relevant column, a digital value to be obtained that represents the amount of charges integrated by the pixel.

As illustrated in FIG. 2, there are therefore two control signals per row R$_i$ of pixels: the signal RS$_{KN_i}$ for initialising photodiodes and the signal Sel$_i$ for selecting reading, applied to the gate, respectively, of the transistor M1 and of the transistor M3 of all the pixels of the row of rank i. These signals are commanded, by a sequencing circuit DM of the sensor, to control a dental radiological image capture sequence, conventionally comprising the following series of phases (see FIG. 4):

a phase 301 of overall initialisation RSG of the photodiodes, i.e. simultaneously applied to all the pixels of the matrix, activated by commanding all the transistors M1 to switch to the ON state at the same time: all the signals RS$_{KN_i}$ (i=1 to N) are activated (set to V$_{ON}$);

an integration phase 302 that starts at the same time for all the pixels, commanded by deactivating all the signals RSKN$_i$ (return to VOFF);

a sequential reading phase 303, by scanning rows of pixels, which starts after an integration duration d$_{INT}$ (elapsed duration since the start of the integration phase). In this phase, the signals Sel$_i$ are activated (set to V$_{ON}$) one after the other (one at a time), during a reading duration d$_r$. The reading circuit RD is generally configured to take two samples: a sample of the signal level (SHS) corresponding to the amount of charges integrated by the photodiode since the start of the integration phase, and a sample of a reference level, after re-initialisation RS$_i$ of the photodiode by activating the initialisation signal RS$_{KN_i}$ of the current row selected for reading. In practice, electrically, the drain electrode d of the initialisation transistor M1 of each of the pixels is connected to a connection node NC common to all the pixels and is usually connected to a reference voltage source VRS, used to re-initialise the photodiodes (discharge all the charges accumulated in the potential well of each photodiode).

Topologically, as shown in FIG. 2, for each pixel, this common connection node NC corresponds to a point of connection, indicated by a black dot, to a conductive gate GRS (shown as a thick line) produced on a conducting topological level of the sensor chip. The term gate is to be understood in terms of a periodic 2D mesh, in step with the matrix. The gate GRS, which is suitably electrically connected to the reference voltage source VRS, allows initialisation of the photodiodes in the overall initialisation phase RSG and in the selective initialisation phases (RS$_j$) RS$_{i+1}$, . . . ) during the sequential reading of the pixels.

According to the invention, and as illustrated in FIGS. 1 and 2, provision is made for the common connection node NC (or the gate GRS) not to be directly connected to the initialisation voltage source VRS, but it is connected to this source VRS by a switching circuit as a function of the logic state "0" or "1" of a control logic signal PROB1. This switching circuit MUX1 comprises two channels for connecting the node NC: a first channel X1 is connected to the source VRS; a second channel X2 is connected at a signal input IN-DTX1 of a current detection circuit DTX1, with a current-voltage converter, of the sensor. The purpose of this circuit DTX1 is to supply a signal OUT-DTX1 as output that indicates the detection of the start of exposure of the sensor to the X-ray flash, when the current I that is produced by all the photodiodes (of the pixels) of the matrix and collected on the common connection node NC, via the initialisation transistors M1 all activated in the on-state and the circuit MUX1, exceeds a predetermined threshold.

Figure 4:
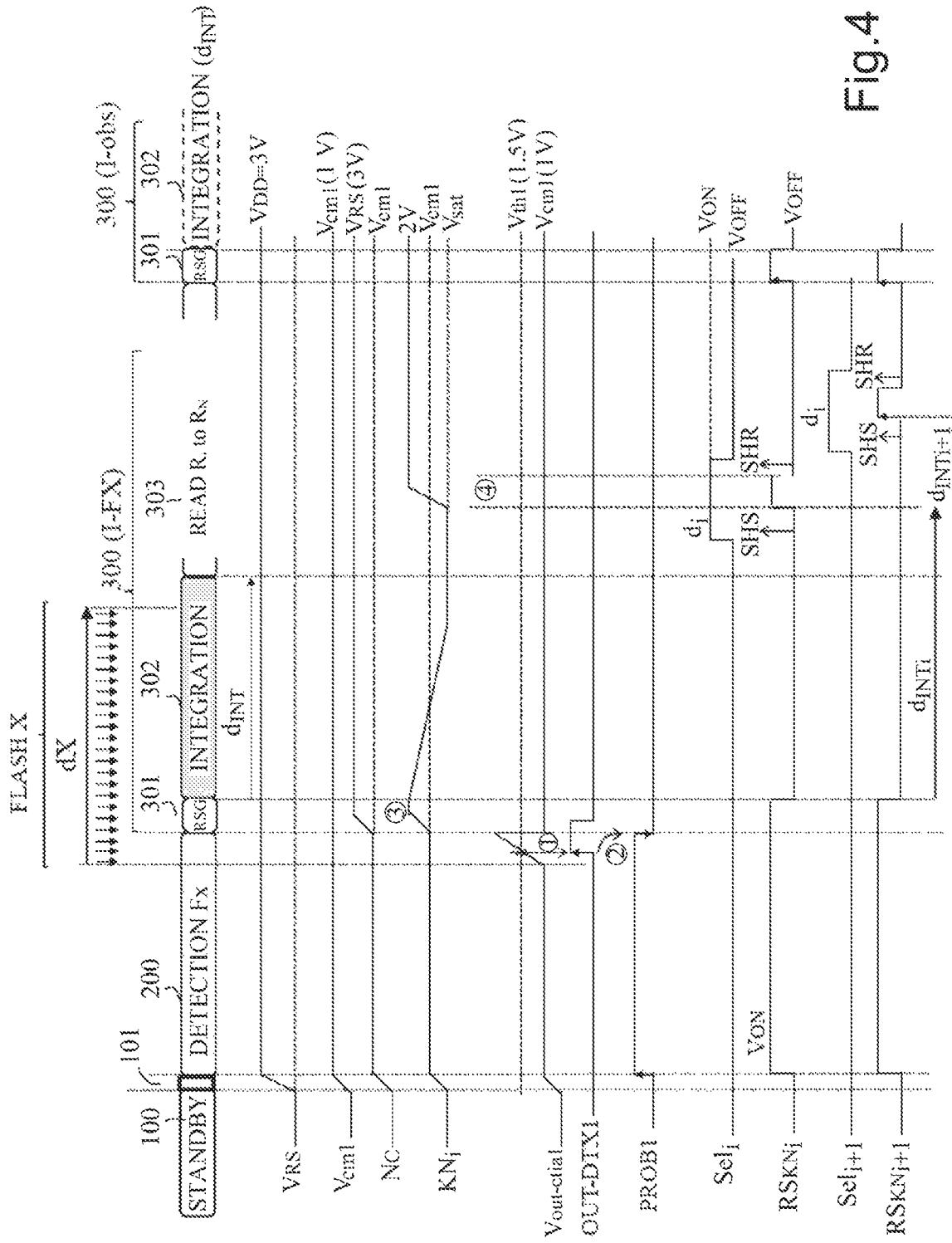
FIG. 4 is a timing chart of the control signals of a phase of detecting the occurrence of an X-ray flash and of an image capture sequence in an image sensor with a start of X-ray flash detection circuit according to the invention.

More specifically, and as illustrated on the timing chart of FIG. 4, the sequencing circuit DM commands a phase 200 of detecting the start of an X-ray flash (on completion of a standby phase STANDBY 100) by the following series of steps:

by placing the signal PROB1 in a first logic state, in the example the high state ("1") for selecting the channel X2 of the switch MUX1: the common connection node NC of all the pixels is then connected to the current input IN-DTX1; and by simultaneously activating all the photodiode initialisation signals RSKN$_i$, allowing the transistor M1 of each pixel to be used as a gate for transferring charges between the photodiode node KN$_i$ (cathode) of the photodiode of the pixel and the common connection node NC. In this way, all the charges from all the photodiodes of the matrix are collected on the node NC, producing the photocurrent I injected at the input IN-DTX1 of the circuit DTX1. It is this that makes the detection of the occurrence of the X-ray flash according to the invention efficient and precise, since it takes into account the current contribution of all the pixels of the photosensitive matrix of the sensor: the matrix of pixels is then used as an immense well of charges for detecting the start of exposure to the X-ray flash. Thus, irrespective of the position of the sensor in the mouth of the patient, there will always be pixels in the matrix for which the X-rays will arrive with little or no attenuation.

When the current detection circuit DTX1 detects that the current passes above a predetermined threshold, the output logic signal OUT-DTX1 changes state: in the example it transitions from the high logic state "1" to the low logic state "0" and it is this that is detected by the sequencing circuit DM, which then triggers an image capture sequence 300:

by placing the signal PROB1 in the other logic state, in the example the low state ("0") for selecting the channel X1 of the switch MUX1: the common connection node NC of all the pixels is then connected to the initialisation voltage VRS;

by keeping the initialisation transistors M1 active for the duration of the phase 301 of overall initialisation RSG.

The other phases of the image capture sequence (integration 302, sequential reading 303) controlled by the sequencing circuit DM then follow in the usual manner. This means that, in the invention, the pixels of the matrix are firstly used as pixels for detecting the start of exposure to the X-ray flash, then as image capture pixels.

Figure 3:
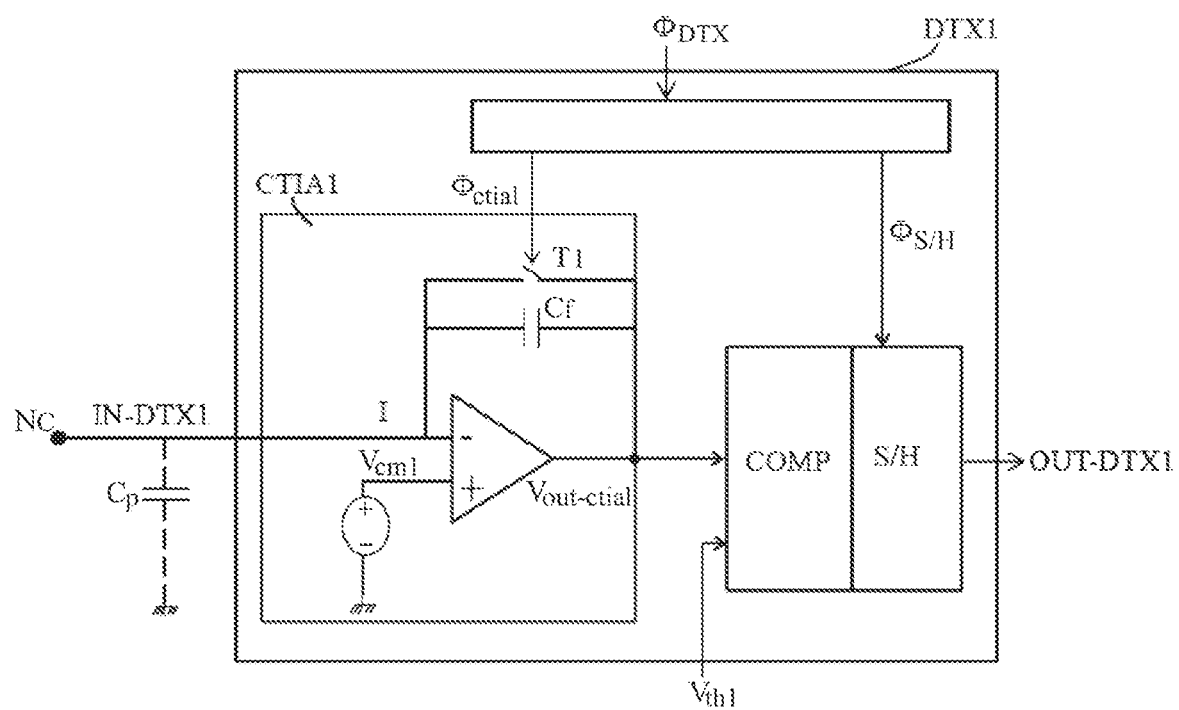
FIG. 3 is a block diagram of a capacitive transimpedance amplifier detection device.

FIG. 3 illustrates an embodiment of a current detection circuit DTX1 allowing implementation of the detection phase 200, comprising a capacitive transimpedance amplifier CTIA1 and a voltage comparator COMP1. It is to be noted that the use of a capacitive transimpedance amplifier is known for integrating the current supplied by detection photodiodes disposed on the edge of the matrix of pixels and for detecting the arrival of an X-ray flash, as described, for example, in the aforementioned application WO2017/121728. These capacitive transimpedance amplifiers are also used for reading infrared sensor pixels, as described, for example, in application EP 1399746.

The capacitive transimpedance amplifier CTIA1 ensures periodic integration of the input current I, at a clock frequency $\Phi_{ctia}$, and it is followed by the voltage comparator COMP1 for comparing the voltage level of the signal $V_{out\text{-}ctia1}$ that it delivers as output to a programmable voltage threshold $V_{th1}$. The voltage comparator is configured to supply a logic signal OUT-DTX1 as output, which toggles from an initial logic state (typically "0") to another state ("1") when the signal level $V_{out\text{-}ctia1}$ exceeds the threshold $V_{th1}$.

The amplifier CTIA1 of FIG. 3 corresponds to a possible embodiment based on a basic configuration of a capacitive transimpedance amplifier, with a feedback loop comprising an initialisation switch T1 placed in parallel on an integration capacitor Cf. However, the invention is not limited to this embodiment and covers other implementations of the prior art.

The noninverting input (+) of the amplifier CTIA1 is connected to a common mode voltage $V_{cm1}$ and the inverting input (−) is the signal input IN-DTX1, through which the current I to be measured is injected. The switch T1 is periodically closed (ON) by an initialisation phase control signal $\Phi_{ctia}$, for discharging the integration capacitor Cf and bringing the output voltage $V_{out\text{-}ctia1}$ and the input IN-DTX1 to the level of the common mode voltage $V_{cm1}$, which is used as a reference point for the periodic integration of the input current I. This integration starts when the switch T1 returns to the open state (OFF) and all the current I injected at the input is integrated in the terminals of the capacitor Cf, with a gain that depends on the ratio between the feedback loop capacitor (Cf in the example) and the capacitor Cp on the signal input, which represents the parasitic capacitance (equivalent) of the photodiodes.

Figure 5:
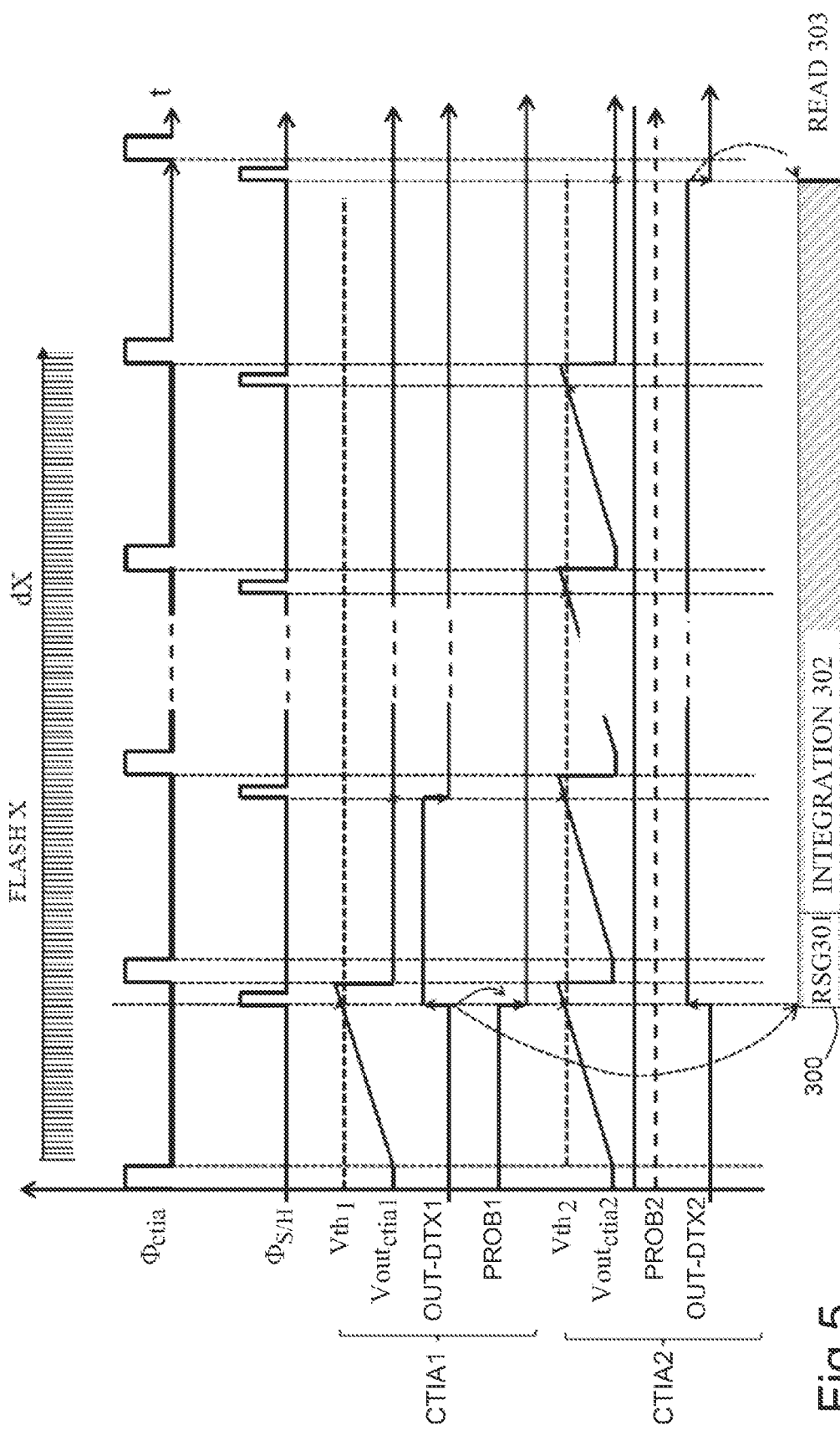
FIG. 5 is a timing chart of the signals of the start of X-ray flash detection circuit, and also those of a detection circuit of the same type, used according to the invention to detect the end of an X-ray flash.

A signal is obtained at the output $V_{out\text{-}ctia1}$ that is a voltage ramp, as illustrated in FIG. 5.

The comparator comprises, for example, an analogue stage of comparing the voltage $V_{out\text{-}ctia1}$ to a configurable threshold value Vali, and a stage of shaping the signal that supplies a logic signal OUT-DTX1 as output. This signal typically toggles from a low state to a high state (FIG. 5), when the voltage $V_{out\text{-}ctia1}$ passes above the threshold $V_{th1}$. It is this toggling that is detected by the sequencing circuit DM for synchronising (triggering) the image capture sequence upon arrival of the X-ray flash.

The sequencing circuit DM then toggles the signal PROB1 to the other logic state ("0" in the example), for selecting the first input channel X1 of the circuit MUX1: the common connection node NC of each pixel is then connected to the initialisation voltage source VRS of the photodiodes. With the transistors M1 being in the on-mode ($RSKN_i$ at VON) they are kept in this mode (FIG. 4), the effect of which is to trigger the phase 301 of overall re-initialisation RSG of the pixels, which is the first phase of the image capture sequence 300(1-FX) during the exposure to the X-ray flash. The sequencing circuit DM subsequently controls the integration phase, which starts at the same time for all the pixels, then the sequential reading phase, in the usual manner. FIG. 4 illustrates a complete sequence of detecting the start of an X-ray flash and of image capture, after the practitioner has positioned the sensor behind the selected anatomical zone, with the active face towards the X-ray source, and has then triggered the source, for example, from a control computer or directly by activating the source. This activation causes the sensor to exit a standby mode 100 (STANDBY) through an activation signal transmitted by the computer and/or the source via a wireless or wired (USB) interface.

The sensor exits the standby mode (Standby) and enters an initialisation phase 101, allowing power supply $V_{DD}$ and reference VRS voltages to be established. The amplifier CTIA1 initialises ($\Phi_{ctia}$, FIG. 5): the voltage at the output $V_{out\text{-}ctia1}$ and at the input IN-DTX1 to the common mode $V_{cm1}$ voltage level of the amplifier, which is at a level above the rest voltage $V_{pin}$ of the photodiodes. In the example, $V_{pin}$ is at 0.8 volts and $V_{cm1}$ is at 1 volt. As illustrated in FIG. 4, this also causes the potential of the common connection nodes NC (the gate GRS) and the nodes $KN_i$ of the photodiodes (cathode) to rise to this same common mode level $V_{cm1}$.

The sequencing circuit DM subsequently controls the phase 200 of detecting the X-ray flash as follows:
  it sets all the rows $RSKN_i$ for controlling the gate of the initialisation transistors M1 to VON; and
  activates the signal PROB1 in the logic state ("1") that selects the second channel X2 of the circuit MUX1, which causes all the common connection nodes NC of the transistors M1 of the pixels (and therefore the conductive gate GRS) to be connected to the input IN-DTX1 of the current detection circuit DTX1.

The signals SELL for selecting reading of the rows of pixels all remain in the inactivated state (low state) for the entire period of the detection phase 200.

When the rays of the flash X-ray reach the active face of the sensor, the photodiodes generate charges, which produces a current I at the input IN-DTX1 that represents the contribution of all the photodiodes of the matrix. This current is integrated by the amplifier CTIA1, which produces a voltage ramp at the output. When the ramp voltage $V_{out\text{-}ctia1}$ exceeds the threshold $V_{th1}$, which is set to 1.5 volts in the example, the output OUT-DTX1 toggles to the high (logic) state (arrow No. 1, FIG. 4), and it is this toggling (detection of a rising edge and/or of the high logic state) of the signal OUT-DTX1 that indicates the detection of the start of an X-ray flash on the sequencing circuit DM. In a non-limiting practical embodiment, the comparator COMP1 includes a latch type output stage activated by a sampling clock $\Phi_{S/H}$ at the same frequency, but in a phase shifted manner, as the clock $\Phi_{ctia}$ (FIG. 5).

When the circuit DM detects toggling of the signal OUT-DTX1 indicating the detection of the start of exposure, it can then control the successive phases of the image capture sequence 300(1-FX) during exposure to the flash, as already explained above:
  the signal PROB1 changes logic state (arrow No. 2). It transitions to "0" in the example, selecting the other channel X1 of the circuit MUX1: the nodes NC (the gate GRS, FIG. 2) are then all electrically connected to the reference voltage source VRS. The input IN-DTX1 is decoupled from the node NC and no longer receives any current. The output voltage $V_{out\text{-}ctia1}$ returns to (and remains at) the common mode voltage level $V_{cm1}$ and re-toggles the output OUT-DTX1 of the comparator COMP1 to the low state (FIGS. 4 and 5);
  the signals $RSKN_i$ for commanding photodiode initialisation to switch to the active state (VDD) are kept in the active state (transistors M1 on) allowing the phase 301 of overall initialisation RSG of the image capture sequence to be carried out: the photodiodes are drained of their charges, and the capacitive nodes $KN_i$ are brought (arrow No. 3) to a voltage level (2 volts in the example) that corresponds to the reference voltage VRS (3 volts) less the threshold voltage of the transistor M1.

The sequencing circuit DM subsequently transitions all the signals $RSKN_i$ to the inactive state (FIG. 4), thus blocking all the transistors M1 and it is this that marks the start of the phase 302 of integrating pixels: the photodiodes begin to integrate charges through the effect of electrical photoconversion and to accumulate these charges (parasitic photodiode capacitance). The potential of the nodes $KN_i$ decreases as a function of the accumulated charges (as a function of the illumination) up to a minimum $V_{sat}$ that corresponds to the saturation of the pixel or of the reading chain.

In the example illustrated in FIG. 4, the sequential reading phase 303 starts after an integration duration $d_{INT}$ that is pre-set to a value above the emission duration dX of the X-ray source that is used. At the end of the duration $d_{INT}$, counted from the start of the integration phase (by a counter of the sequencing circuit DM, for example), the sequencing circuit DM activates the sequential reading phase 303, allowing the pixels of each of the N rows of the matrix to be read row-by-row.

Taking the row of pixels $R_i$: the signal $SEL_i$ for selecting this row is activated to switch the selection transistor M3 of each of the pixels of this row to the on-state (ON), for a reading duration $d_r$: for each pixel of the row, the voltage level supplied by the transistor M2, which corresponds to the amount of charges accumulated at this moment in the photodiode (capacitive reading node $KN_i$), is transferred to the column conductor $Col_j$ of the pixel (via M3) in order to be sampled (SHS) by a respective reading circuit RD; then the photodiode of each of the pixels of the row is re-initialised by activating the signal $RSKN_i$ for re-initialising this row only (it can be seen that the signal $RSKN_{i+1}$ of the next row $R_{i+1}$ remains inactivated at this moment) and a new voltage level that is a re-initialisation level is transferred to the column conductor $Col_j$, and sampled (SHR) by the reading circuit. The difference between the signal level and the re-initialisation level represents the image data supplied by the pixel. The same reading sequence is repeated for each of the rows of the matrix successively.

The sequencing circuit DM is generally configured to control, following a first radiological image capture I-FX sequence 300, a second dark noise I-obs image capture sequence 300 by applying the same integration duration $d_{INT}$, for measuring a dark current level when the sensor is no longer exposed to the X-ray. The image data of the dark noise I-obs are subsequently subtracted point-by-point from the data of the first image. A better quality radiological image is obtained.

As the integration duration $d_{INT}$ is set (which means that there is no end of X-ray flash detection in the sensor), the second sequence 300(I-obs) may only be carried out episodically, in order to take into account any variations, in particular of temperature, and not systematically, each time a radiological image is taken. Between two refreshes, the image data of the dark noise are stored, for example, in a memory circuit associated with the control circuit DM, and subtracted from the obtained radiological image data.

The invention has been explained for a 3T pixel sensor, but it can be extended to active pixels using more than three transistors, allowing the same integration duration to be applied to all the pixels, through the presence of a reading node separated from the photodiode node by at least one transfer transistor. In this way, the effects of the dark noise in the image are reduced.

Figure 6:
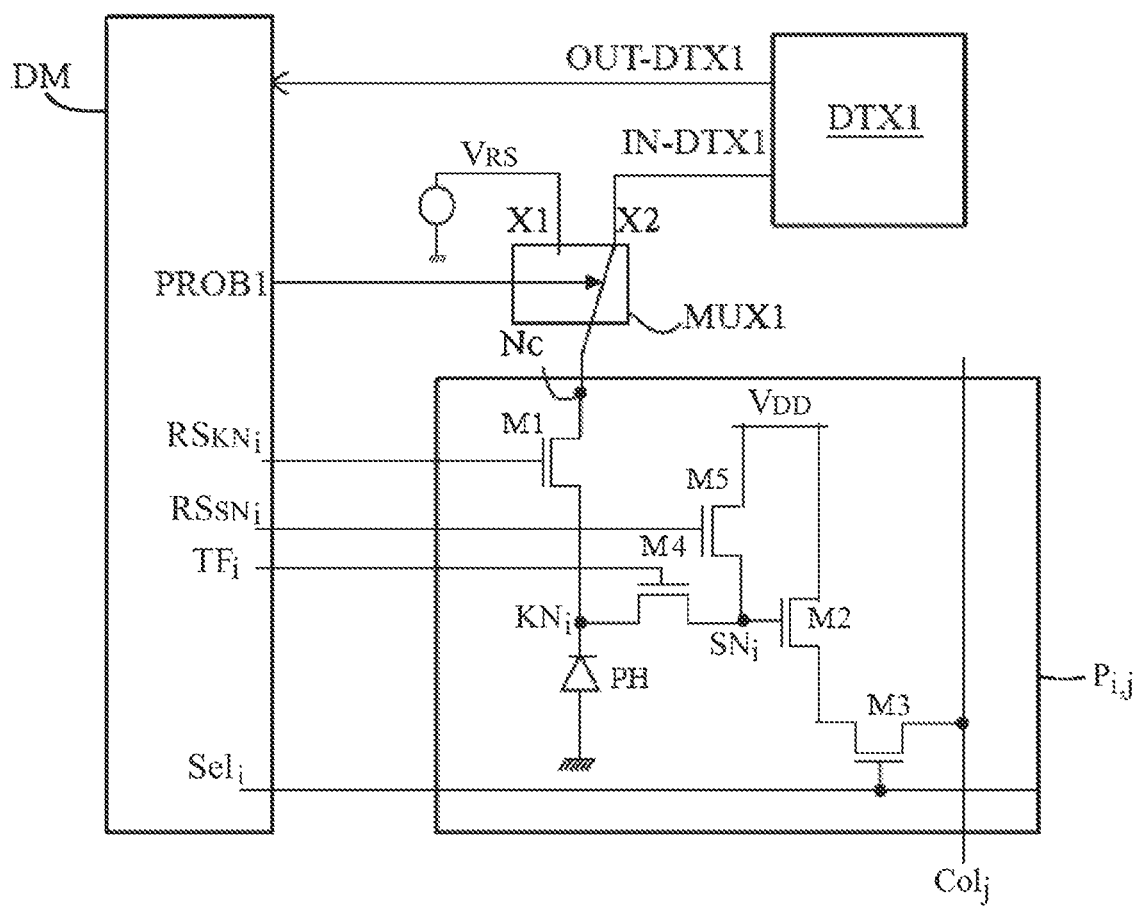
FIG. 6 is a functional block diagram of the invention applied to an active pixel of the five transistor (5T) type, at least.

The invention is particularly applicable to 5T pixels (understood as comprising at least 5 transistors), which comprise, as for the 3T pixels, an initialisation transistor M1 specific to the photodiode, as illustrated in FIG. 6. The invention is thus implemented in the same manner, with the current detection circuit DTX1 and the circuit MUX1 allowing the common connection node NC to be firstly connected to the signal input IN-DTX1 of the circuit DTX1 during a phase of detecting the start of exposure to an X-ray flash, then to the reference voltage source Vrs allowing the photodiodes to be initialised before a phase of integrating an image capture sequence triggered by this detection.

Compared to the 3T pixel of FIGS. 1 and 2, it is to be noted that the 5T pixel (FIG. 6) further comprises a capacitive reading node $SN_i$ (typically a floating diffusion) that is separated from the photodiode node $KN_i$ by a transfer transistor gate, denoted M4, controlled by a transfer control signal $TF_i$. This signal is activated to transfer the charges integrated by the photodiode to the reading node. It is thus possible to control an overall transfer phase, commanded by the transistor M4 in all the pixels simultaneously, which marks the end of the current integration phase in all the pixels, before the sequential reading phase. The 5T pixel also comprises an initialisation transistor M5 of the reading node $SN_i$: it is this transistor M5 that is activated, in the phase of reading the pixel, by a control signal denoted $RSSN_i$, before sampling SHR a corresponding re-initialisation level, to be subtracted from the signal level (SHS).

In an alternative embodiment of the invention, applicable to the pixels with three or more transistors, the same principle for current detection of the start of exposure to the X-ray flash is used to also detect the end of exposure to the X-ray flash, which then determines the end of the integration period. This allows the integration duration of the pixels to be adjusted as closely as possible to the actual duration dX of the flash, allowing the integrated dark current level to be reduced.

Figure 7:
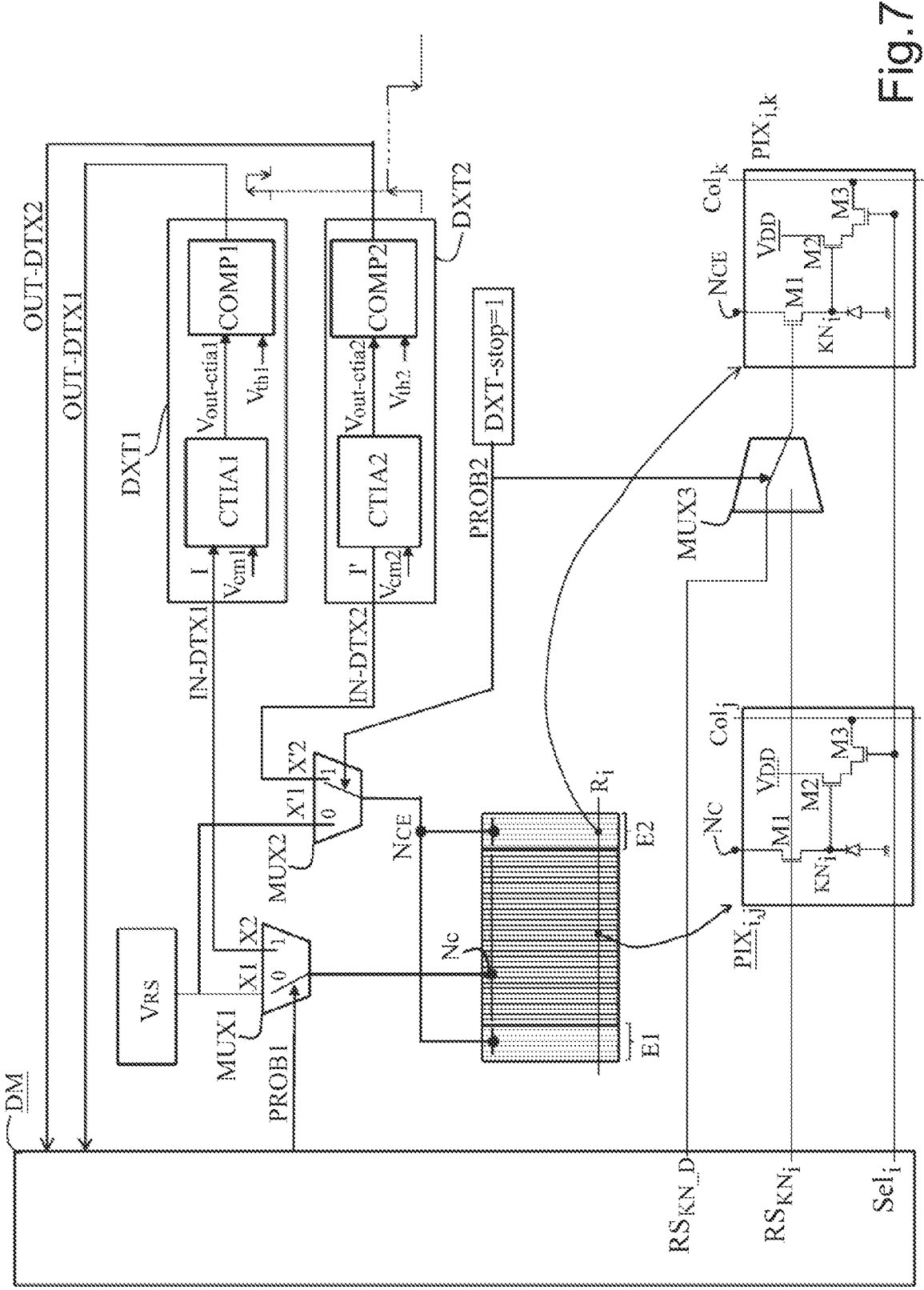
FIG. 7 is a block diagram of a 3T pixel sensor according to one embodiment of the invention allowing detection of the start and end of an X-ray flash.

More specifically, according to the invention, this end of exposure detection according to the invention is carried out by a detection circuit DTX2 similar to the circuit DTX1, but on the basis of a current I' produced by a set of pixels of the matrix configured as detection pixels. As illustrated in FIGS. 7 (3T pixels) and 8 (5T pixels), these pixels are coupled to a different common connection node NCE, electrically isolated from the node NC, and the sensor comprises a second detection circuit DTX2 for receiving the current I' photogenerated by the pixels coupled to the node NCE. This circuit DTX2 comprises a capacitive transimpedance amplifier CTIA2 and a comparator COMP2 for comparing to a configurable voltage threshold $V_{th2}$. The two detectors can operate at the same operating frequency ($\Phi_{ctia}$). The two amplifiers CTIA1 and CTIA2 in principle have the same common mode voltage ($V_{cm1}=V_{cm2}$).

Topologically, in this alternative embodiment, it is then possible to have two conductive gates isolated from each other, one that interconnects the nodes NC and the other that interconnects the nodes NCE.

As shown by the timing charts of FIG. 5, in the phase of detecting the start of exposure, the two detection circuits DTX1 and DTX2 operate in a similar manner, one integrating a current I originating from the pixels of the matrix used for image capture and the other integrating a current I' originating from pixels of the matrix configured as detection pixels (this will be explained hereafter). In the two circuits, the amplifier produces an output voltage ramp, and the outputs OUT-DTX1 and OUT-DTX2 of the comparators toggle, to "1" in the example, once the ramp voltage passes above the comparison threshold ($V_{th1}$, $V_{th2}$).

Figure 9:
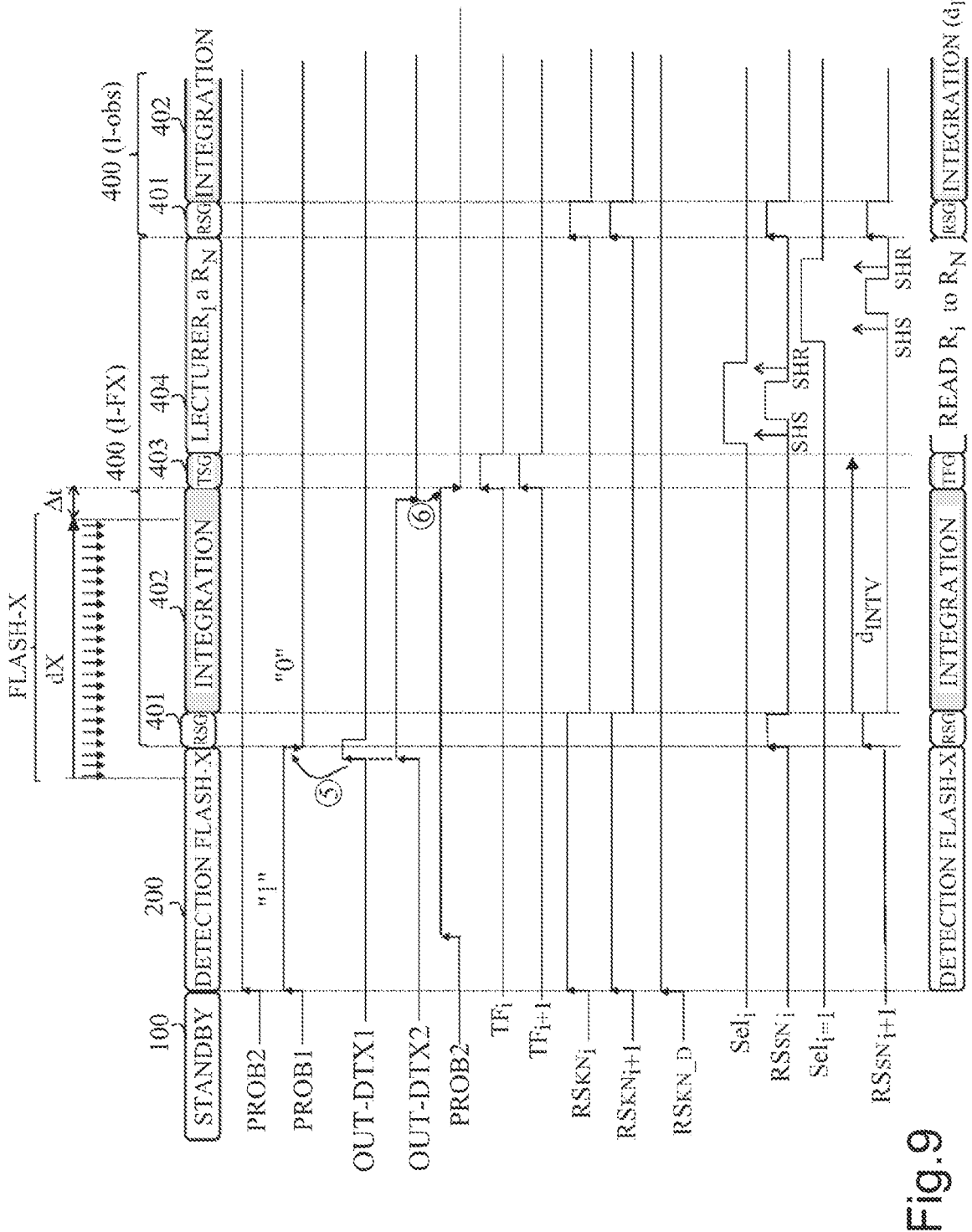
FIG. 9 is a timing chart of the control signals for radiological image capture according to the invention, including the detection of the start and end of an X-ray flash, respectively for triggering and stopping the phase of integrating a radiological image capture sequence.

The circuit DTX1 for detecting the start of an X-ray flash is then decoupled from the node NC (through the action of the signal PROB1): the amplifier CTIA1 of the detection circuit DTX1 no longer receives current as input: the output voltage $V_{out\text{-}ctia1}$ remains at the level of the common mode voltage $V_{cm1}$ and at the output of the comparator COMP1 the signal OUT-DTX1 toggles back, to the "0" state in the example. The pixels of the matrix coupled to the node NC are then used to carry out an image capture sequence; the sequencing circuit controls, as has been seen, firstly the phase of overall re-initialisation RSG of the photodiodes, then activates the integration phase (FIG. 9).

As long as the sensor is exposed to the X-ray flash, the detection circuit DTX2 continues to receive a current I' photogenerated by the pixels of the matrix coupled to the node NCE: the amplifier CTIA2 continues to produce a periodic voltage ramp as output, which exceeds the threshold $V_{th2}$. The output OUT-DTX2 of the comparator COMP2 therefore remains unchanged, at "1" in the example.

The end of exposure to the X-ray flash is expressed by a current I' that practically no longer increases: the slight increase is associated with the dark current in the photodiodes. The ramp voltage then passes below the threshold $V_{th2}$: the signal OUT-DTX2 toggles back, to the "0" state in the example. It is this toggling that is detected by the sequencing circuit DM and is used to stop the phase of integrating the current image capture sequence.

The number of pixels of the matrix used to detect the end of exposure can be lower, compared to the total number of pixels, at a ratio of 1 to 2000. In practice, this is taken into account by adjusting the gains of the amplifiers CTIA1 and CTIA2 and/or by using different comparison thresholds ($V_{th1}$, $V_{th2}$) in the comparators COMP1 and COMP2. It is also possible to reduce the operating frequency ($\Phi_{ctia}$, $\Phi_{S/H}$) of the second detector (CTIA2, COMP2): the speed of detecting the end of exposure may not be as good since the patient is no longer irradiated.

The number of pixels of the matrix used to detect the end of exposure can be less than the total number of pixels, for example, in a ratio of 1 to 2000. It is also possible to adjust the gains of the amplifiers CTIA1 and CTIA2 and/or to use different comparison thresholds ($V_{th1}$, $V_{th2}$). It is also possible to reduce the operating frequency of the second detector (CTIA2, COMP2). The speed of detecting the end of exposure may not be as good since the patient is no longer irradiated.

In practice, the detection pixels, coupled to the nodes NCE can be the pixels of some columns and/or rows of pixels of the matrix, and/or of pixels dispersed in the matrix). In the example illustrated in FIGS. 7 and 8, the pixels that are used to detect the end of an X-ray flash are the pixels of the first columns (set E1) and of the last columns (set E2) of the matrix. To simplify the representation of the drawing, the sets E1 and E2 are successive columns on each matrix edge (successive rows could have been used). However, in practice, rows and/or columns interleaved with "normal" pixel columns preferably would be selected for image capture: for example, one column in two or 4 from among the 20 first columns and the 20 last columns of a matrix that comprise several hundred columns; or even pixels dispersed throughout the entire matrix would be selected. Indeed, for the pixels used for end of X-ray flash detection, the signal is lost for reading. Image information needs to be reconstituted for each of the end of flash detection pixels by interpolation on the basis of the neighbouring pixels. Therefore, it is better for these detection pixels to be spaced apart from each other in order to limit any interpolation errors.

The connection node NCE common to the pixels used for end of flash detection is connected to the input IN-DTX2 of the circuit DTX2, while the pixels of the matrix coupled to the node NC are used in a current image capture sequence and this common connection node NC is connected to the voltage reference source (VRS).

During the current image capture sequence, the transistors M1 of the pixels coupled to the node NCE must be kept in the on-state, to allow collection and injection of the current I' originating from the photodiodes of these pixels in the circuit DTX2, whereas the transistors M1 of the pixels coupled to the node NC and carrying out the current image capture are deactivated at the end of the phase of overall initialisation RSG to allow integration of charges.

For the pixels coupled to the node NCE, a signal, denoted RSKN_D, is therefore provided for controlling separate transistors M1, which signal is the same for all these pixels. This signal RSKN$_D$ is activated as soon as the sensor exits standby and remains active at least until the end of exposure is detected.

The end of exposure signal OUT-DTX2 is used by the sequencing circuit DM to terminate the integration phase in the current image capture sequence: it is this signal OUT-DTX2 that thus sets the effective integration duration, $d_{INTV}$, in the current radiological image capture sequence I-FX.

Figure 8:
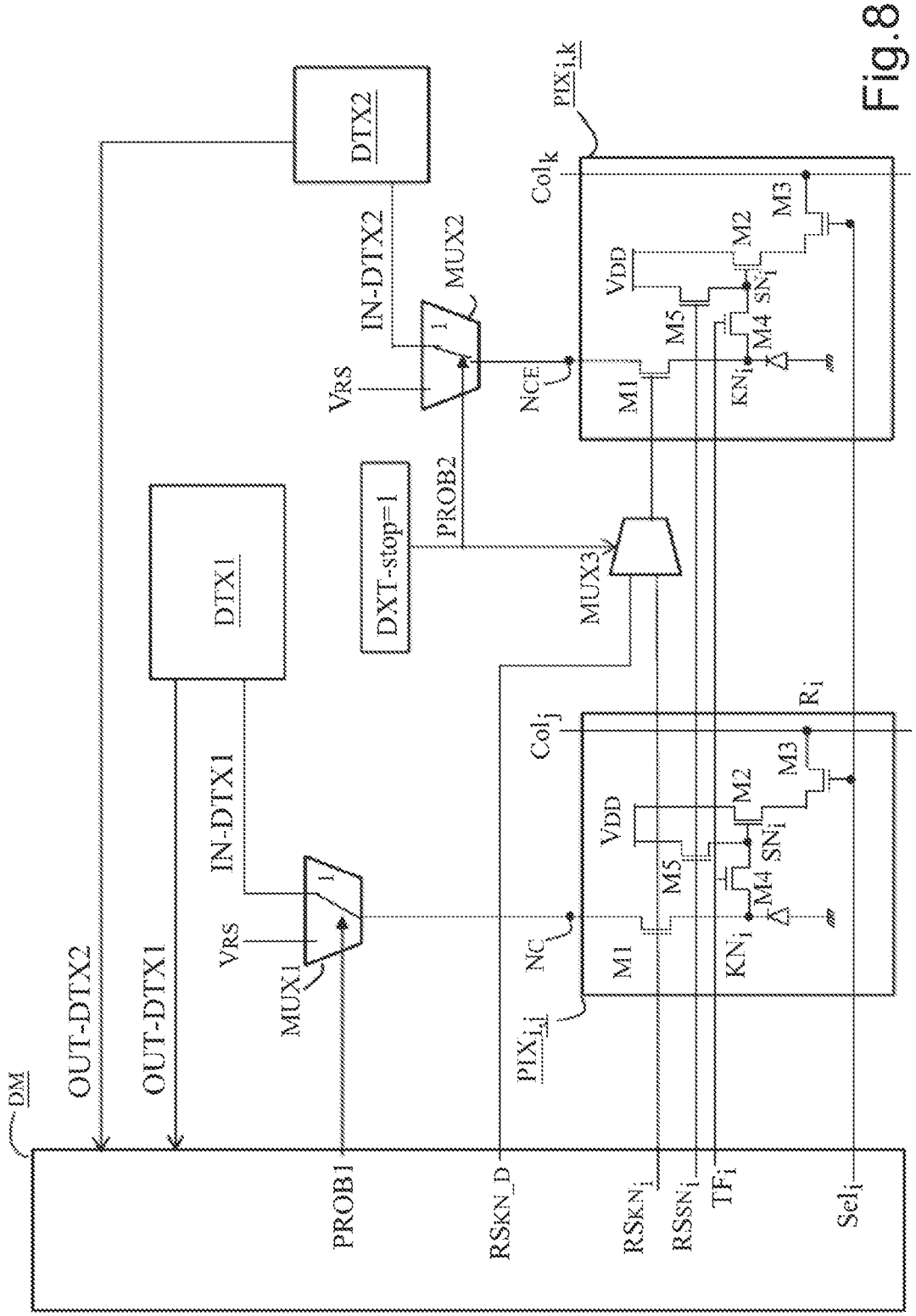
FIG. 8 is a block diagram of a 5T pixel sensor corresponding to this embodiment of FIG. 7.

As illustrated in FIGS. 7 and 8, provision advantageously can be made for the end of exposure detection to be an optional function in the sensor, by providing a multiplexer MUX2 controlled by a logic control signal PROB2, for coupling the node NCE either to the input IN-DTX2 of the circuit DTX2 (channel X'2), and the associated pixels are then used as end of X-ray flash detection pixels, or even to the voltage reference source VRS (channel X'1), and the associated pixels are then used as image capture pixels only. The logic state of the signal PROB2 is then configured by the operator, typically in a register of parameters of the sensor, for activating or not activating the end of X-ray flash exposure detection function. For example, as illustrated, a register of parameters contains a DTX-stop bit to be configured, for example, to 0 so as not to activate the end of exposure detection option, and to 1 so as to activate said option, which positions the logic signal PROB2.

In this case, the transistors M1 of the pixels coupled to the node NCE need to be suitably controlled according to whether they are used for end of exposure detection or as image capture pixels. For example, a logic circuit can be provided, as illustrated in the figures, such as a multiplexer MUX3, controlled by this same signal PROB2, so that:
  when the detection option is deactivated, PROB2 is at 0 and the transistor M1 of each pixel coupled to the node NCE is controlled by the control signal RSKN$_i$ corresponding to the row of the pixel in the matrix;
  when the detection option is activated, PROB2 is at 1, the transistors M1 of the pixels coupled to the node NCE are all controlled by the control signal RSKN_D.

FIGS. 7 and 8 show that the principle of detecting end of exposure according to the invention that has just been described is similarly applicable to a 3T or 5T pixel sensor.

FIG. 9 more specifically shows the timing chart of the signals for detecting the start and end of exposure to the X-ray flash, and of associated control signals in the event that the end of exposure detection is implemented (PROB2="1" in the example). In the example, the I-FX and I-obs image capture sequences 400 comprise an overall transfer phase 403 for transferring the charges to the reading nodes $SN_i$ of the pixels, before the sequential reading phase 404, corresponding to a 5T pixel image sensor, as illustrated in FIG. 8. With a 3T pixel sensor as illustrated in FIG. 7, this overall transfer phase 403 does not exist and the end of exposure detection triggers the sequential reading phase 404.

For the (I-FX or I-obs) image capture sequence 400 controlled by the sequencing circuit DM, after detection of the start of exposure (arrow No. 5), the phase 401 of overall initialisation RSG activates all the signals $RSKN_i$ (i=1 to N) simultaneously to initialise the photodiode nodes $KN_i$ of the pixels coupled to the node NC; the signal RSKN_D for initialising the photodiode nodes $KN_i$ of the pixels coupled to the node NCE; and all the signals $RSSN_i$ simultaneously for initialising the reading nodes $SN_i$ of all the pixels of the matrix (whether they are coupled to the node NC or NCE).

The end of exposure detection (arrow No. 6) triggers the overall transfer phase 403 TFG for transferring charges from the photodiode nodes $KN_i$ to the reading nodes $SN_i$, which is simultaneously applied by the transistors M4 of the 5T pixels to all the image capture pixels (signals $TF_i$). It is this that sets the integration duration, the same for all the pixels: same start, corresponding to the end of the phase RSG, when the signals $RSKN_i$ are simultaneously deactivated, and same end, corresponding to the end of the phase TFG, when the signals $TF_i$ are simultaneously deactivated. The phase 404 of reading pixels begins. The row of rank i selected for reading this phase includes sampling (SHS) the signal level of the pixels of the row; re-initialisation of the reading node $SN_i$, by activating the signal $RSSN_i$ of the row before sampling (SHR) the corresponding reference level. It is to be noted that the obtained data stream includes the data of the pixels coupled to the node NCE that have been used to detect the end of exposure: the data obtained (read) for these pixels will not be used in practice, but will be replaced by data computed by interpolation. This does not change anything in the sequence; this is taken into account in the image processing.

It is to be noted that the effective integration duration no longer has a set value that is determined (adjusted) in advance: it is a value $d_{INTV}$ that is defined from the two detection signals OUT-DTX1 and OUT-DTX2. Therefore, it needs to be measured if the intention is to apply the same integration duration in the image capture sequence I-obs of the dark noise. The sequencing circuit then comprises a counter for measuring the effective exposure duration $d_{INTV}$ between the end of the phase 301 of overall re-initialisation RSG of the photodiode nodes $KN_i$ and the detection of the end of the flash (OUT-DTX2) that triggers the reading phase (3T pixels) or the global transfer phase TFG (5T pixels).

As the duration $d_{INTV}$ can potentially vary on each new exposure to an X-ray flash, the dark current image capture is systematic.

In practice, the sequencing circuit DM applies filters to the detection signals OUT-DTX1 and OUT-DTX2, allowing elimination, i.e. not taking into account, of the spurious pulses that particularly would be induced when switching channels in the circuit switching circuits MUX1 and MUX2, by the variations in potential induced on the connection nodes NC or NCE and on the photodiode nodes $KN_i$. Also, the circuit DM can thus filter to ignore the signal OUT-DTX1 during the image capture sequences 300, and filter to ignore the signal OUT-DTX2 during the phases 200 of detecting the start of flash exposure. These various filtering measures ("anti-glitch" filters) are common measures implemented to avoid false detections.

The invention that has just been described allows the quality of radiological images, in particular dental images, to be improved at less expense, since they use the pixels of the matrix and the current detection circuits that are known to a person skilled in the art.

The invention claimed is:

1. Intraoral radiological image sensor using MOS technology comprising:
    a matrix (M-PIX) of first photosensitive pixels arranged in rows and columns, each pixel ($P_{ij}$) comprising a photodiode (PH) and a plurality of transistors, the plurality of transistors including a photodiode initialisation transistor (M1) connected between a photodiode node ($KN_i$) of the pixel and a first connection node (NC) common to the first photosensitive pixels;
    a sequencing circuit (DM) supplying signals for commanding the plurality of transistors of each of the first photosensitive pixels for controlling an image capture sequence (300) during exposure to an X-ray flash (FX), comprising a phase of overall initialisation (301) of the photodiodes of the first photosensitive pixels, a phase of integrating charges (302) during an integration period and a phase of reading (303) the first photosensitive pixels;
    wherein the sensor comprises a first coupling switch (MUX1) controlled by a first logic signal (PROB1) for connecting said first connection node (NC) to a signal input (INDTX1) of a first current detection circuit (DTX1) or to a photodiode initialisation voltage source (VRS), whereby said first logic signal is changeable between a first logic state and a second logic state;
    the sequencing circuit (DM) of the sensor being configured to control a phase (200) of detecting, by said first detection circuit (DTX1), the start of exposure to an X-ray flash for triggering the image capture sequence (300), comprising the following operations:
        commanding the photodiode initialisation transistors (M1) to switch to the on-state in all the first photosensitive pixels simultaneously; and
        establishing the first logic signal (PROB1) in said first logic state, the effect of which is to inject, at the signal input (IN-DTX1) of the first detection circuit, a current (I) collected on said first connection node (NC) originating from the photodiodes of the first photosensitive pixels; then
        establishing, when an output logic signal (OUT-DTX1) of the first detection circuit toggles from a first output logic signal state to a second output logic signal state, corresponding to the detection of an input current level above a predetermined threshold, the first logic signal (PROB1) in said second output logic signal state, the effect of which is to couple said initialisation transistors (M1), which are always in the on-state, to said initialisation voltage source (VRS), thus activating the phase of overall initialisation (301) of the image capture sequence, for initialising the photodiodes before said integration phase; and
    wherein the first detection circuit (DTX1) comprises a capacitive transimpedance amplifier (CTIA1) comprising a noninverting input connected to a common mode voltage (Vcm1) and an inverting input, which forms the signal input (IN-DTX1), which is coupled to said first connection node (NC), said amplifier being controlled by a clock signal ($\Phi_{ctia}$) for periodically producing, at a signal output ($V_{out\text{-}ctia1}$) of said amplifier, a voltage ramp as a function of the level of the current injected at the signal input, which ramp is applied to a comparator (COMP1) for comparison to a voltage threshold value ($V_{th1}$).

2. Image sensor according to claim 1, wherein each of the first photosensitive pixels comprises said photodiode initialisation transistor (M1), a voltage follower transistor (M2), a gate of which is connected to the photodiode connection node ($KN_i$), and a reading selection transistor (M3) connected in series between said voltage follower transistor (M2) and a respective column conductor ($Col_j$) connected to a pixel reading circuit (RD).

3. Image sensor according to claim 1, wherein each of the first photosensitive pixels comprises said initialisation transistor (M1), a charge transfer transistor (M4) connected in series between said photodiode connection node ($KN_i$) and a pixel reading node ($SN_i$), an initialisation transistor (M5) of the reading node, a transistor (M2) mounted as a voltage follower, a gate of which is connected to said reading node ($SN_i$) and a reading selection transistor (M3) connected in series between said voltage follower transistor (M2) and a respective column conductor ($Col_j$) connected to a pixel reading circuit (RD).

4. Image sensor according to claim 1, wherein the image sensor further comprises a set (E) of second photosensitive pixels including a photodiode initialization transistor (M1) connected between a photodiode node ($KN_i$) of the pixel and a second connection node (NCE), which is electrically isolated from said first connection node, the sensor further comprising a second current detection circuit (DTX2) of the same type as said first detection circuit wherein both the first current detection circuit (DTX1) and the second current detection circuit (DTX2) are controlled by a clock signal ($\Phi_{ctia}$), an input signal (IN-DTX2) of which is coupled to said second connection node (NCE), the sequencing circuit (DM) of the sensor being configured for, in said phase (200) of detecting the start of exposure:
  commanding the initialisation transistors (M1) of all of the first photosensitive pixels of the matrix, and the second photosensitive pixels of said set (E) coupled to the second connection node, to switch to the on-state; and
  upon detection of the toggling of an output signal (OUT-DTX1) of the first detection circuit (DTX1):
    keeping the initialisation transistors (M1) of the second photosensitive pixels of said set (E) in the on-state, at least until the toggling of the output signal (OUT-DTX2) of the second detection circuit is detected that corresponds to a current injected at the input, collected on said second connection node (NCE) that passes below a predetermined threshold; and
    stopping, upon detection of the toggling of said output signal (OUT-DTX2) of the second detection circuit indicating the detection of the end of exposure to the X-ray flash, the phase of integrating the image capture sequence (300) for initiating the reading phase.

5. Image sensor according to claim 4, comprising a second coupling circuit (MUX2) allowing the second connection node (NCE) to be connected to the signal input (IN-DTX2) of the second detection circuit or to the initialisation voltage source (VRS) controlled by a second control logic signal (PROB2), which is configured in the sensor for configurable configuration of the second photosensitive pixels of said set (E) into end of exposure detection pixels or into image capture pixels.

6. Image sensor according to claim 4, wherein the first detection circuit (DTX1) comprises a capacitive transimpedance amplified (CTIA1) comprising a noninverting input connect to a common mode voltage (Vcm1) and an inverting input, which forms the signal input (IN-DTX1), which is coupled to said first connection node (NC), said amplifier being controlled by the clock signal ($\Phi_{ctia}$) for periodically producing, at a signal output ($V_{out\text{-}ctia1}$) of said amplifier, a voltage ramp as a function of the level of the current injected at the signal input, which ramp is applied to a comparator (COMP1) for comparison to a voltage threshold value ($V_{th1}$).

7. Image sensor according to claim 6, wherein a gain of the capacitive transimpedance amplifier and/or the voltage threshold value of the comparator are adjustment parameters of the sensor adjusted in said first detection circuit and in said second detection circuit for respectively detecting a start and an end of an X-ray flash.

8. Image sensor according to claim 1, wherein the sequencing circuit (DM) is configured to trigger another image capture sequence (300(I-obs)) applying an integration duration ($d_{INT}$, $d_{INTV}$) and using the same first photosensitive pixels for the image capture as a preceding image capture sequence (300(I-obs)) carried out during exposure to the X-ray flash and having supplied first image data, allowing measurement and subtraction of dark noise on said first image data.

9. Radiological image capture method using an intraoral radiological image sensor using MOS technology, said sensor comprising a matrix (M-PIX) of first photosensitive pixels arranged in rows and columns, each pixel ($P_{ij}$) comprising a photodiode (PH) and transistors, including a photodiode initialisation transistor (M1) connected between a photodiode node ($KN_i$) of the first photosensitive pixel and a first connection node (NC) common to the first photosensitive pixels, wherein the method comprises, in a first phase (200), coupling said first connection node (NC) to a signal input (IN-DTX1) of a current detection circuit (DTX1) provided in the sensor for detecting when a current injected at the signal input (IN-DTX1) exceeds a predetermined threshold, corresponding to the detection of the start of exposure to an X-ray flash, said detection triggering an image capture sequence (300) with the effect of coupling said first connection node (NC) to a voltage source (VRS) allowing a phase of overall initialisation of the photodiodes (301), before an integration phase (302) during an integration duration, then a phase of reading the first photosensitive pixels (303);
  wherein the current detection circuit (DTX1) comprises a capacitive transimpedance amplifier (CTIA1) comprising a noninverting input connected to a common mode voltage (Vcm1) and an inverting input, which forms the signal input (IN-DTX1), which is coupled to said first connection node (NC), said amplifier being controlled by a clock signal ($\Phi_{ctia}$) for periodically producing, at a signal output ($V_{out\text{-}ctia1}$) of said amplifier, a voltage ramp as a function of the level of the current injected at the signal input, which ramp is applied to a comparator (COMP1) for comparison to a voltage threshold value ($V_{th1}$).

10. Radiological image capture method according to claim 9, allowing control of the integration duration, in a current image capture sequence, by an end of exposure detection signal that is supplied by another current detection circuit (DTX2) of the sensor, which has a signal input (IN-DTX2) coupled to a second connection node (NCE), which is electrically isolated from said first connection node and which is connected to the initialisation transistors (M1) of a set (E) of second photosensitive pixels, said other current detection circuit (DTX2) having a signal output configured to activate the end of exposure detection signal (OUT-DTX2) when the current (I') originating from the photodiodes of the second photosensitive pixels of said set (E) passes below a predetermined threshold.

11. Radiological image capture method according to claim 10, wherein the control of the integration duration by an end of exposure detection signal is activated or deactivated by a second configurable control logic signal (PROB2) applied to a second coupling circuit (MUX2) allowing the second connection node (NCE) to be connected to the signal input (IN-DTX2) of the second detection circuit or to the initialisation voltage source (VRS).

12. Radiological image capture method according to claim 9, wherein the one or more current detection circuits provided in the sensor are of the capacitive transimpedance amplifier and comparator type.

\* \* \* \* \*